United States Patent [19]

Durette

[11] Patent Number: 4,866,036
[45] Date of Patent: Sep. 12, 1989

[54] DIPEPTIDYL 5-0,6-0-ACYL-2-AMINO-2-DEOXY-D-GLUCOFURANOSE COMPOSITIONS AND METHODS OF USE IN AIDS-IMMUNOCOMPROMISED HUMAN HOSTS

[75] Inventor: Philippe L. Durette, New Providence, N.J.

[73] Assignee: Merck & Co., Inc., Rahway, N.J.

[21] Appl. No.: 105,057

[22] Filed: Oct. 5, 1987

[51] Int. Cl.$^4$ ............... A61K 37/02; A61K 39/00; C07C 103/52
[52] U.S. Cl. ............................. 514/8; 514/9; 514/21; 514/42; 514/44; 514/46; 514/50; 514/75; 514/78; 514/357
[58] Field of Search ............... 424/88, 89, 92, 85, 424/177; 514/8, 2, 9, 21; 530/322; 548/535; 524/42, 44, 46, 50, 75, 78, 357; 260/396 R

[56] References Cited

U.S. PATENT DOCUMENTS 4,310,514  1/1982  Durette ....................... 424/88

OTHER PUBLICATIONS

Dagani; "Efforts Intensify to Develop Drugs, Vaccine that Combat Aids," C & E News, Dec. 8, 1986, pp. 7–14.

Primary Examiner—John Kight
Assistant Examiner—Nathan M. Nutter
Attorney, Agent, or Firm—Robert J. North; John W. Harbour

[57] ABSTRACT

Disclosed are specific dipeptidyl 5-0, 6-0-Acyl-2-amino-2-deoxy-D-glucofuranoses, which, either alone, or in combination with an anti-AIDS drug, e.g. azidothymidine, provide protection in human individuals whose resistance to infection has been specifically suppressed by an AIDS-related (HIV) virus, as well as help to suppress the AIDS-related infection itself.

5 Claims, No Drawings

DIPEPTIDYL 5-0,6-0-ACYL-2-AMINO-2-DEOXY-D-GLUCOFURANOSE COMPOSITIONS AND METHODS OF USE IN AIDS-IMMUNOCOMPROMISED HUMAN HOSTS

BACKGROUND OF THE INVENTION

1. Field of the Invention

This invention relates to dipeptidyl 5-0, 6- 0-acyl-2amino-2-deoxy glucofuranoses which alone, or in combination with an anti AIDS drug, e.g. azidothymidine, protect against opportunistic infection in a human host immunocompromised as a result of an AIDS related viral infection.

2. BRIEF DESCRIPTION OF DISCLOSURES IN THE ART

The search for new immunostimulants capable of augmenting host defenses to combat infection, cancer and congenital immunodeficiency disorders is an increasingly important area of pharmaceutical endeavor particularly as it relates to AIDS related viruses.

Seven years ago few had ever heard of acguired immune deficiency syndrome, or AIDS. This puzzling affliction, then seen in only a small number of young, homosexual men, was something new and unnamed. Today, it's hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, acguired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, currently designated HIV-I (human immunodeficiency virus) and also known as lymphadenopathy-associated virus (LAV) (Barré Sinoussi et al., Science 220: 868 (1983)). Similar viruses have been reported by other scientific groups (Popovic et al., Science 224: 497 (1984); Levy et al. Science 225: 840 (1984)) and designated human T-cell lymphotropic virus type III (HTLV-III), AIDS-associated retrovirus (ARV), or immune deficiency associated virus (IDAV). Still more recent data indicates that LAV, HTLV-III, ARV and IDAV share several important characteristics, including substantial nucleotide homology (Wain Hobson et al., Cell 40: 9 (1985); Muesing et al., Nature (1985); Sanchez-Pescador et al , Science 227: 484 (1985)), and should be considered isolates of the same virus, although there is a likelihood that strain to strain variations among the viral isolates will exist. In addition to exhibiting substantial nucleotide homology, the isolates are similar with respect to morphology, cytopathology, reguirements for optimum reverse transcriptase activity, and at least some antigenic properties (Levy, supra: Schupbach et al., Science 224: 503 (1984)). The above materials are hereby incorporated by reference to characterize the phrase "AIDS related virus".

U.S. Pat. No. 4,310,514 to Durette (assigned to Merck & Co., Inc.) describes immunologically active dipeptidyl 5-0, 6-0-acyl- 2-amino- 2-deoxy-Dglucofuranoses, described herein, and their methods of preparation, which reference is hereby incorporated by reference for this particular purpose.

However, the above disclosure does not specifically describe the use of the compounds alone, or in combination with an anti AIDS drug, e.g. azidothymidine, as host resistance enhancing agents, i.e., immunostimulators specifically to combat opportunistic viral, fungal and bacterial infections in human AIDS immunocompromised hosts.

SUMMARY OF THE INVENTION

In accordance with the present invention there is provided a method for enhancing host resistance to opportunistic infection in an AIDS-immunocompromised human host comprising the step of administering to said host a composition containing a compound of the formula (I):

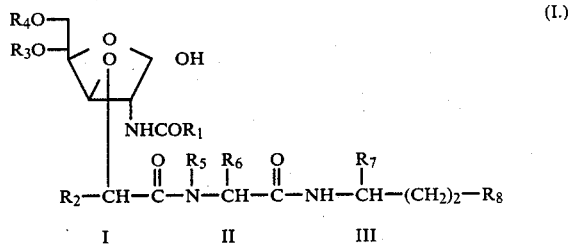

wherein:

$R_1$ is $C_{1-7}$ alkyl, substituted $C_{1-7}$ alkyl; phenyl; or substituted phenyl;

$R_2$ is hydrogen; or $C_{1-10}$ alkyl;

$R_3$ and $R_4$ may be the same or different and are each independently acyl of the formula:

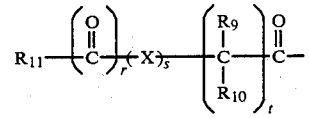

where X is —O—, —S—, or

$R_9$, $R_{10}$, and $R_{12}$ may be the same or different and are each independently hydrogen; $C_{1-20}$ alkyl; $C_{1-20}$ alkyl carbonyloxy; amino; benzyl; $C_{1-20}$ alkoxymethyl; or $C_{1-20}$ alkylamido;

r is 0 or 1; s is 0 or 1; and t is 0–20, provided that s may only be 0 when r and t are greater than 0, or when r is 0 and $R_{11}$ is amino, phenyl, substituted phenyl, 1-adamantyl, or heterocycle selected from the group consisting of 2- or 3 furyl, 2 or 3-thienyl, 2- or 3-pyrrolidinyl, 2, 3-, or 4-pyridyl, and 1-tetrazolyl, said heterocycle optionally substituted with $C_{1-20}$ alkylcarbonyl; and $R_{11}$ is hydrogen; $C_{1-30}$ alkyl; $C_{2-30}$ alkenyl; $C_{1-30}$ alkoxy; phenyl; $C_{1-20}$ alkylsulfonyl; or cholesteryl; and $R_4$ may additionally be hydrogen;

$R_5$ is hydrogen; or together is $-CH_2-CH_2CH_2$;

$R_6$ is hydrogen; $C_{1-7}$ alkyl; hydroxymethyl; mercaptomethyl; benzyl; or substituted benzyl;

$R_7$ and $R_8$ be the same or different and are each independently COOR or CONR'R", where R is hydrogen or $C_{1-7}$ alkyl, and R' and R" are each independently hydrogen or $C_{1-3}$ alkyl;

when $R_2$ is $C_{1-10}$ alkyl, the stereochemistry at asymmetric center I can be either D or when $R_6$ is not hydrogen, the stereochemistry at asymmetric center II is L; the stereo chemistry at asymmetric center III is D; and pharmaceutically acceptable salts thereof; in a physiologically acceptable medium, in an amount effective to impart resistance against viral, bacterial, and fungal infection in an AIDS-immunocompromised human host.

Also provided is a composition containing the above-described compounds in combination with an anti AIDS drug for enhancing host resistance in a human AIDS-immunocompromised host.

Specifically provided is where the composition contains an anti-AIDS drug selected from one or more of the following: azidothymidine, AL 721, ampligen, ansamycin, azimexon, cyclosporine, foscarnet, HPA-23, imreg-1, inosine pranobex, alpha-interferon, interleukin-2, D-penicillamine, ribavirin, suramin, CS 85, 2', 3'-dideoxycytidine, 2', 3'-dideoxyadenosine, gamma interferon, RNA deriv, lobulin IG-IV, thymopentin, thymostimulin, methionine enkephalin or eguivalents thereof.

Also provided is a method for enhancing resistance to bacterial, viral or fungal infection in a human host immunocompromised by an AIDS-related virus comprising administering to said host a pharmaceutical composition, as described above, in which method, the anti AIDS drug can be administered in combination, concurrently or separately, with the indicated compound.

DESCRIPTION OF THE INVENTION AND PREFERRED EMBODIMENTS

The compositions described herein provide very high levels of protection against opportunistic infections in immunocompromised animals and humans.

By the term "AIDS related virus" is meant the commonly designated HIV series (human immuno deficiency virus) formerly called HTLV and LAV, and species thereof, as described above in the indicated incorporated references.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "immunostimulant", as used herein, is meant a material which can be employed to potentiate a non-specific immune response on the part of the host.

The composition of the present invention does not contain specific antigens per se. Rather, the composition contains only immunostimulants for producing a generalized and nonspecific immunological response on the part of the host, and further includes acceptable salts, carriers, diluents, vehicles and the like for intravenous, subcutaneous or intraperitoneal administration.

The term "substituted alkyl" for $R_1$ refers to an alkyl group of from 1 to 7 carbon atoms substituted by hydroxy, mercapto, alkoxy of 13 carbons, alkylmercapto of 13 carbons, hydroxy or mercapto esterified by an acid of 1–4 carbon atoms, halogen (F, Cl or Br), carboxyl, or carboxyl functionally modified by esterification with a lower alcohol of 1–3 carbons or by amidation. Preferably, the alkyl substituents are hydroxy or mercapto, either free or substituents by an alkyl group of 1-3 carbons.

The substituents in the term "substituted phenyl" for $R_1$ refer to the phenyl group substituted by one or more alkyl groups of 1 3 carbon atoms or hydroxy or mercapto groups either free, or etherified by an alkyl group of 1–3 carbons or esterified by an acid of 1–4 carbons, lower (1–4C) alkyldioxy, cycloalkyldioxy of 5–7 carbon atoms, amino, trifluoromethyl, halo, or phenyl.

The substituents in the term "substituted phenyl" for $R_{11}$ are halo or phenyl.

$R_7$ and $R_8$, among the optionally esterified 10 carboxyl groups can be mentioned the carboxyl group esterified by a lower alcohol of 1–3 carbons, like methanol or ethanol. The carboxyl group can also be amidated, unsubstituted at the nitrogen atom or mono- or di-substituted with an alkyl, in particular, a lower alkyl, an aryl, particularly phenyl, or an aralkyl, particularly benzyl.

Most preferably, $R_1$ is alkyl of 1–3 carbons, phenyl or phenyl p-substituted by alkyl (1–3C), amino, halogen, hydroxy or trifluoromethyl;

$R_6$ is preferably hydrogen, alkyl of 1–4 carbons, hydroxymethyl, mercaptomethyl, benzyl or p-hydroxybenzyl; and preferably $R_5$ and $R_6$ together are $-CH_2CH_2CH_2-$.

The obtained compounds can be transformed to their salts in a classical fashion, for example, by reacting the acidic compounds obtained with alkaline or alkaline earth hydroxides, or the basic compounds with acids.

The Formula I compounds can be used in the form of salts derived from inorganic or organic acids. Included among such salts are the following: acetate, adipate, alginate, aspartate, benzoate, benzene sulfonate, bisulfate, butyrate, citrate, camphorate, camphorsulfonate, cyclopentanepropionate, digluconate, dodecylsulfate, ethanesulfonate, fumarate, gluco heptanoate, glycerophosphate, hemisulfate, heptanoate, hexanoate, hydrochloride, hydrobromide, hydroiodide, 2-hydroyethanesulfonate, lactate, maleate, methanesulfonate, 2-naphthalenesulfonate, nicotinate, oxalate, pamoate, pectinate, persulfate, succinate, tartrate, thiocyanate, tosylate, and undecanoate. Also, the basic nitrogen-containing groups can be guaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil-solulle or dispersible products are thereby obtained.

The compounds in the present invention possess immunostimulatory properties and may be used as immunomodulating agents, i.e. to stimulate the host immune response. They are especially useful for increasing the host response against viral infections.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or poly ethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilized preparations that contain the active ingredient alone or together with a carrier, for example mannitol, for these to be manufactured before use. The mentioned solutions or suspensions may contain viscosity increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or vials and the sealing of the containers.

Furthermore, the compounds of the present invention provide, alone, or in combination with "anti AIDS drugs", human host protection against opportunistic infections in individuals immunocompromised by an AIDS related infectious organisms in addition to direct therapeutic effect against the AIDS-related virus. These include fungal, viral and bacterial, including the specific conditions of Kaposi's sarcoma and pneumocystis pneumonia. They are also capable of potentiating antibiotic activity.

By the term "anti AIDS drugs" is meant therapeutic drugs which are thought to act directly or indirectly against the AIDS related virus by a variety of known or unknown mechanisms.

The following anti-AIDS drugs are currently being investigated and are known to exhibit either some antiviral or immunomodulatory effect in a human host against the AIDS related virus (from *Chemical & Engineering News*, Dec. 8, 1986, pp 7–14, hereby incorporated by reference for this purpose):

AL 721. Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six week clinical trial.

Ampligen. Mismatched double stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$). Italian antibacterial drug, a member of the rifamycin group of antibiotics, which are characterized by a natural ansa structure (chromophoric naphthohydro guinone group spanned by a long aliphatic bridge). Drug has shown some efficacy in treating AIDS patients with an opportunistic infection caused by the bacterium *Mycobacterium aviumintracellulare*.

Azidothymidine (AZT, 3'-azido 3'-deoxythymidine, zidovudine). First drug to show promise in prolonging lives of patients with AIDS or AIDS related complex (ARC). Well absorbed orally and effectively penetrates central nervous system, but has relatively short half-life in the body and some toxicity, with anemia and headaches. ARC patients treated with AZT showed virtually no toxic effects.

Azimexon. Cyanaziridinyl immunemodulator. Early trial showed improvements in symptoms and immune function in patients with ARC but not AIDS; only toxic effect was mild hemolysis (disintegration of red blood cells with release of hemoglobin), which disappeared when treatment ceased.

Cyclosporine (cyclosporin A). Cyclic undecapeptide with potent immunosuppressive effects, used in cancer therapy. Inhibits T4 lymphocyte dependent immune responses. Basis of controversial AIDS therapy in France; rationale is that HIV infects "activated" T4 cells, which are primed to defend the body, so drug that prevents activation of T4 cells may limit progression of disease. The French claim encouraging results with it.

Foscarnet (trisodium phosphonoformate). Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV infected patients.

HPA 23 (ammonium 21-tungsto-9 antimoniate, $[(NH_4)_{18}(NaW_{21}Sb_9O_{86})_{17}]$. Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg-1. Proprietary immunemodulator derived from white blood cells. Reportedly can enhance production of other biological response modifiers such as interleukin-2 and $\gamma$-interferon, which are critical to normal functioning of immune system.

Inosine pranobex (isoprinosine, inosiplex). p-Acetamidobenzoic acid salt of (1 dimethylamino-2 propanol:inosinate complex 3:3:1 molar ratio). Chemically synthesized antiviral and immune modulator originally developed to enhance memory in elderly. In one study, found to improve immune function in ARC patients.

$\alpha$-Interferon. Glycoprotein produced by cells in response to virus infection; helps amplify or regulate immune responses. Checks the growth of HIV in vitro. Has induced tumor regression in some AIDS related Kaposi's sarcoma cases. Not known whether $\alpha$-interferon has anti-HIV activity in vivo.

Interleukin- 2 (IL-2). Protein made by white blood cells that mediates production of interferon. Inability to produce IL-2 may predispose AIDS patients to opportunistic infections. Preliminary results of therapy with recombinant IL-2 not encouraging, but trials continue.

D-Penicillamine (3-mercapto-D-valine). Used to treat rheumatoid arthritis and Wilson's disease, a rare copper-storage disease. Inhibits HIV reproduction in humans. In trials at George Washington Universiety Medical Center, it suppressed the virus but also temporarily depressed T cell levels in 13 AIDS patients with perpetually swollen glands.

Ribavirin ($1\beta$- D ribofuranosyl 1,2,4-triazole 3-carboxamide). Synthetic nucleoside used to treat a viral respiratory infection in children. In early clinical trials, it inhibited viral replication and improved immune function in AIDS patients. Longer (24 week) trial in 373 ARC patients has been completed; at 12 weeks, ribavirin's safety profile was judged to be acceptable, and the drug was found to be well tolerated.

Suramin ($C_{51}H_{34}Na_6O_{23}S_6$)Antiparasitic agent. Potent inhibitor of HIV reverse tran scriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the U.S. Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
| --- | --- |
| Immunomodulators | |
| Thymopentin | Ortho Pharmaceuticals |
| Thymostimulin | Sereno Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |
| Immune globulin IG-IV | Sandoz Pharmaceuticals and Alpha Therapeutics |

[1] a subsidiary of Praxis Pharmaceutical;

Further, Yakult's immunostimulant, LC-9018, and two herbal products, shosaikoto and ginseng, being studied by Tsumura Juntendo, may be of benefit in patients with AIDS.

LC-9018 has been foud to be about 20 times more potent than Ajinomoto's lentinan in inducing macrophage activation, and it is undergoing clinical trials in AIDS patients in the U.S. Phase III trials with LC-9018 in patients with cancer are currently underway in Japan. Shosaikoto and ginseng have been found to increase depleted helper T-cell counts in seven of nine AIDS carriers studied by researchers at Tsumura Juntendo and Tokyo Medical University.

Furthermore, HEM Research's potential anticancer agent, ampligen (a mismatched double-stranded RNA), reduces at least five fold the concentration of Wellcome's azidothymidine (Retrovir) reguired for inhibitory activity against human immunodeficiency virus (HIV) in vitro, (The Lancet Apr. 18th, p. 890). Ampligen is currently in Phase II clinical trials as an anticancer agent and HEM is seeking partners to fund a clinical trial in AIDS.

At higher concentrations of azidothymidine, there seemed to be a synergistic relation between the two compounds, since complete protection was provided by combined suboptimal doses of each drug. Ampligen could reduce the dose of azidothymidine reguired for a therapeutic effect in vivo, so reducing its toxicity.

Since the two drugs have entirely different modes of action, it is unlikely that they will exert toxicities other than those associated with each drug alone. In recent clinical studies, "virtually no toxicity" was asociated with intravenous ampligen. Moreover, since ampligen has clinically demonstrated immunological as well as antiviral activity, its use together with azidothymidine may have pronounced and long term beneficial effects on the course of AIDS beyond that which can be estimated in vitro.

In addition, CS-85, or 3'azido 2', 3'-dideoxy-5 ethyl-(uridine), developed by Raymond F. Schinozi at the Veterans Administration Medical Center and Emory University, both in Atlanta, Ga. shows promise.

All of the above described compounds are deemed to be included ithin the scope of the term "anti AIDS drus" as used herein. Use of more than one of these compounds, in addition to the glyocopeptide of structure I, in the combination composition is contemplated.

The composition containing the glycopeptide compounds and an above-described anti AIDS drug will contain the glycopeptide in an amount as described above and the anti-AIDS drug in an amount, based on the glycopeptide, in a weight ratio of 1:3 to 3:1 and preferably 1:1 based on the weight of glycopeptide.

The dosage form of the combination drug will be 1 to 50 mg/kg of human body weight per day and preferably 2.5 to 40 mg/kg.

The method of co-administering the two ingredients, if not using the combination composition, can be separately, concurrently or simultaneously.

The obtained compounds can be transformed to their salts in a classical fashion, for example, by reacting the acidic compounds obtained with alkaline or alkaline earth hydroxides, or the basic compounds with acids.

The present invention is also directed to pharmaceutical preparations that contain a compound of Formula I. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, n the form of unit doses like tablets, capsules, suppositories, and ampoules.

Also a subject of the invention is a method for administering to an immunocompromised host a composition as described herein, containing a compound of the formula I, as described, contained in a suitable carrier which may or may not have additional material such as diluents and other materials which may be deemed necessary under the circumstances. However, it is understood that the immunostimulatory preparation does not in fact include a specific antigen as a composition component.

The following examples exhibit the subject invention as contemplated by us and should not be construed as being limiting with respect to the scope and nature of the instant invention.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood sample are taken and analyzed for anti-BSA-antibody titers by the passive hemagglutination technigue. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the anitgen, contrary to other bacterial immmunostimulants (like LPS of *E. coli*). The injection of the compounds of the present invention results in augmentation of anti-BSA antibody titer only in mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long lasting immunostimulatory effects on systemic activation of immune apparatus.

2. Stimulation of Mitotic Responses of Lymphocyte Cultures

Mouse lymphoid cells are cultured in micro titer plates, in RPMI 1640 medium with 2% fetal calf serum. Cultures are set in triplicates and consist of $3-5 \times 10^5$ spleen or $1.5 \times 10^6$ thymus cells per well in a final volume of 0.2 ml. Class specific mitogens are added at optimal or suboptimal concentrations, while control cultures are incubated without mitogens. The tested compounds are added shortly after the mitogens and the cultures are incubated for 48 hours at 37° with 5% $CO_2$. Incorporation of tritiated thymidine is determined after a pulse (1.0 μCi/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal speen). The effects of the compounds are dose dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as protective agents against infections caused by bacteria, viruses or pathogenic parasites, owing to immunity by humoral antibodies and/or to cellular mediation.

These compounds are therefore especially indicated for stimulation of individual immune defense, e.g., at the time of chronic or acute infections or in cases of selective (antigen specific) immunological deficiencies as well as in situations of immunedeficiency, but also acguired general deficiency (i.e., not antigen-specific) as appears with age, during initial shock from a grave illness, and before and soon after radiation therapy or immunosuppressive hormones. The said compounds can subsequently be administered in combination with anti-infectious antibiotics, chemical therapeutics or other methods of treatment, to combat immunological deficiencies. The described compounds are thus indicated egually for general prophylaxis of infectious disease in man and animal.

Intermediates for the compounds of Formula I may be prepared by condensing, using conventional procedures, a protected compound of Formula II with a protected compound of Formula III.

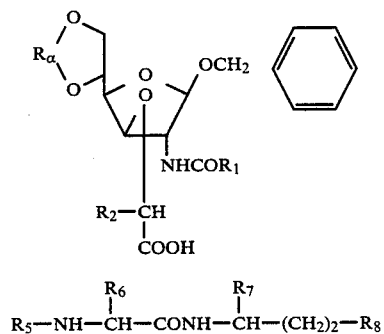

(II.)

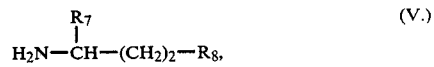

(III.)

In the foregoing Formulas, $R_1$, $R_2$, $R_5$, $R_6$ $R_7$, and $R_8$ represent the groups mentioned above while $R_\alpha$ is an optionally substituted alkylidene radical that blocks the oxygen atoms at the C-5 and C-6 positions. Among the alkylidene radicals, particularly suitable are the lower alkylidene radicals, especially ethylidene, isopropylidene, propylidene, or cycloalkylidene, especially cyclopentylidene, or cyclohexylidene, and also, the optionally substituted benzylidene radical, preferentially substituted at the para position. As protecting group for the carboxyl in the dipeptide of Formula III, there may be mentioned tertiary butyl, benzyl, or benzhydryl. The protecting group may be any suitable to protect the group to which it is attached during the condensation reaction, and which may be readily removed thereafter.

The condensation is effected by reacting the compound of Formula II in the form where the carboxylic acid is activated, with the amino compound of Formula III. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxymethyl ester, the p-nitrophenyl thioester, the p-nitrophenyl ester, the 2,4,5-trichlorophenyl ester, the pentachlorophenyl ester, the N-hydroxysuccinimide ester, the N-hydroxyphthalimide ester, the 8-hydroxyguinoline ester, the 2-hydroxy-1,2-dihydro-1 carboethoxyguinoline esters, the N-hydroxypiperidine ester or enol ester derived from N-ethyl-5-phenyl-isoxazolium 3'-sulfonate. The activated esters may egually be obtained from a carbodiimide by addition of N-hydroxysuccinimide or from a substituted 1-hydroxybenzotriazole for example, a halogen, methyl, or methoxy substituted 3-hydroxy- 4-oxo-3,4-dihydrobenzo[d]-1,2,3-triazine.

The amino group may be activated, for example, by reaction with a phosphitamide.

Among the methods of reaction with the activated esters, one must mention in particular those that involve N-ethyl-5-phenyl-isoxazolium-3'-sulfonate (Woodward's Reagent K), N ethoxy-carbonyl 2-ethoxy-1,2dihydroquinoline, or carbodiimide.

The starting materials utilized are known or can be made in a known fashion. Thus, one can obtain compounds of formula II, for example, by reacting the corresponding sugar unsubstituted at position-3 with a halogen $R_2$ acetic acid where $R_2$ has the meaning mentioned above. The ether is obtained in the presence of a strong base. The halogen is preferentially bromo or chloro.

Another process of synthesizing intermediates for the compounds of Formula I consists of condensation of a protected compound of Formula IV:

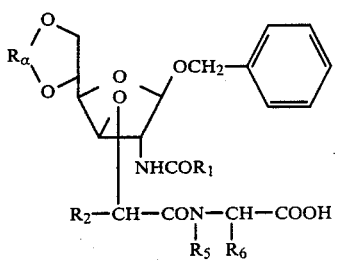

(IV.)

wherein $R_1$, $R_2$, $R_5$, $R_6$, and $R_\alpha$ have the meaning mentioned above, with a compound of Formula V:

$$H_2N-\underset{\underset{R_7}{|}}{CH}-(CH_2)_2-R_8,$$ (V.)

wherein $R_7$ and $R_8$ have the meaning mentioned above.

The condensation may be effected by reacting a compound of Formula IV in the form of an activated carboxylic acid, with the amino compound of Formula V, or by reacting the Formula IV compound in the form of the free C-terminal carboxyl group with the Formula V compound where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore, react the corresponding sugar unsubstituted at position- 3 with halogen-$R_2$-acetamido $R_6$-acetic acid or a compound of Formula II with an amino-$R_6$-acetic acid where the carboxyl group is blocked as mentioned above.

Another process for inserting the side chain at position-3 of the sugar radical consists in reacting a compound having the following structure:

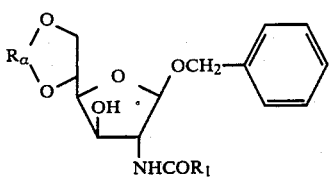

where $R_1$ and $R_\alpha$ have the meaning mentioned above, with a compound of formula VII:

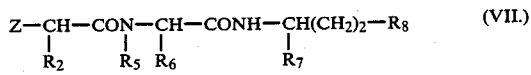

where Z represents an esterified hydroxy group capable of reacting and wherein $R_2$, $R_5$, $R_6$, $R_7$ and $R_8$ have the meaning given above. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. The starting materials utilized are known or can be made in a known fashion.

Condensations of (a) protected compounds of Formula II with a protected compound of Formula III; (b) protected compound of Formula IV with a protected compound of Formula V; or (c) a protected compound of Formula VI with a protected compound of Formula VII, afford intermediates of Formula VIII:

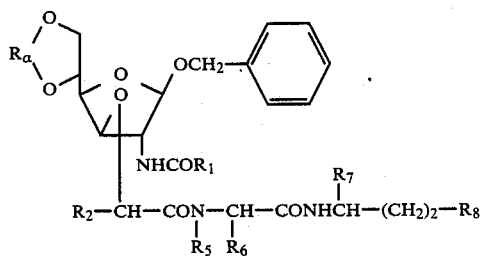

wherein $R_1$, $R_2$, $R_5$, $R_6$, $R_7$, $R_8$, and $R_\alpha$ have the meanings mentioned above.

Intermediates of Formula VIII are converted into compounds of Formula I by selective removal of $R_\alpha$, acylation of the C-5 and C-6 hydroxyls, and final removal of the remaining protecting groups by hydrogenolysis with hydrogen in the presence of a noble metal catalyst.

$R_\alpha$ is removed by acid hydrolysis to give intermediates of Formula IX, which is effected in a classical fashion, for example, with acidic ionexchange resins, in particular, with an exchange resin containing sulfonic acid groups, e.g. Amberlite IR-120 (resins of styrene containing strongly acidic sulfonyl groups) or Dowex-50 (polystyrene sulfonic acids); or with a strong inorganic or organic acid, e.g. hydrochloric acid, hydrobromic acid, sulfuric acid, a sulfonic acid, e.g. methanesulfonic acid, a phenylsulfonic acid optionally substituted in its aromatic nucleus, e.g. p-toluenesulfonic acid, or a carboxylic acid, e.g. acetic acid or trifluoroacetic acid:

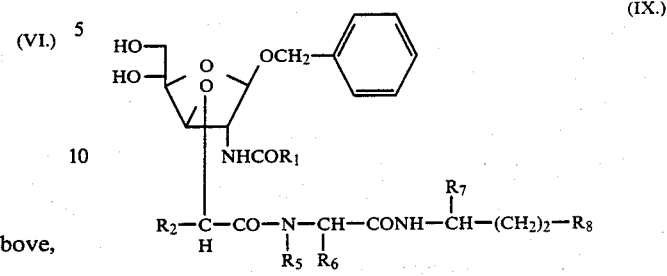

The compounds of Formula I are then prepared by reaction of the intermediates of Formula IX described above with the appropriate acid derivative whereby condensation results in the desired 6-O-and/or 5-O-substituted compounds. All of the appropriate acids for preparing the compounds of Formula I are known compounds or may be prepared by known methods in an obvious manner. The condensation reaction will initially take place preferentially at the 6-position of the glucofuranose ring. Then the reaction conditions are driven with the same or a different acid giving rise to 5-O-, 6-O- diacylated derivatives wherein the acyl groups are the same or different. Where it is desired to prepare only the 5-O-acylated derivatives, the 6-position must be blocked while the 5-position substitution is carried out, followed by deblocking. The blocking and deblocking reactions may be carried out in accordance with procedures well known in the art.

The condensation reactions may be carried out in accordance with procedures well established in the art for preparing organic compounds. Thus, the condensation may be carried out using the carboxylic acid, the acid anhydride, or the acid halide.

Where the carboxylic acid is utilized, a coupling agent, for example N,N'-dicyclohexylcarbodiimide (DCC) in the presence of 4dimethylaminopyridine (DMAP), will be employed. The reaction is carried out in an inert aprotic solvent, such as dimethylformamide, dimethylsulfoxide, or pyridine, at a temperature of from 0° to 50° C. for from 6 hours to 6 days.

Where the acid anhydride is utilized, a coupling agent may be employed, although this is not necessary. However, an acid acceptor, such as pyridine, 4-dimethylaminopyridine, or triethylamine should be used. The solvent medium in which the reaction is carried out and the other reaction conditions are the same as for the carboxylic acid condensation.

Where the acid halide is utilized, all of the reaction conditions are the same as those for the acid anhydride condensation.

Once the condensation reaction has been completed, the remaining protecting groups are readily removed by hydrogenolysis, preferably carried carried out with a catalyst such as palladium oxide in the presence of glacial acetic acid.

Compounds wherein Rhd 1 is other than methyl are obtained by reacting 2-amino-2deoxy-D-glucose, in the case where $R_1$ is alkyl or substituted-alkyl, with the appropriate alkanoic anhydride or alkanoyl halide, preferably chloride, or substituted-alkanoic anhyride or substituted-alkanoyl halide, preferably chloride, and in the case where $R_1$ is phenyl or substituted-phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups are then introduced at the C-1, C-5, and C-6 positions to give a compound of Formula VI which may then be converted to a compound of Formula II or Formula IV.

Compounds wherein $R_6$ is other than methyl, may be obtained when, for example, one of the following amino acids is substituted for alanine:

| Amino acid | $R_6$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_5$ and $R_6$ together are —$Ch_2CH_2Ch_2$ are obtained by substituting proline for alanine.

EXAMPLE 1

Preparation of 2-Acetamido-5,6di- -O- acetyl 2deoxy 3-O-(D2-propionyl-L alanyl D isoglutamine) D-gluco-furanose Step A: Preparation of benzyl 2-acetamido- 3(D- -O-1-carboxyethyl)-2-deoxy- 5,6 -isopropylideneβ-D-glucofuranoside To a stirred solution of benzyl 2-acetamido-2 deoxy-5,6-0 isopropylidene -β-D- glucofuranoside [prepared by the process set forth in A. Hasegawa, T. Sakurai, & N. Hasegawa, Carbohydr. Res., 45 (1975) 19–27](1.88 g., 5.35 mmol) in dry p-dioxane (75 ml.) was added sodium hydride in oil suspension (1.0 g.) (50% of sodium hydride by weight). The mixture was stirred at 95° C. and additional dioxane (70 ml.) was added to break up the gel that formed after addition of the sodium hydride. After 1 hr., the temperature was lowered to 65° C., and a solution of L-2-chloropropionic acid (1.16 ., 10.7 mmol) in a small volume of dioxane (3 ml.) was added. The reaction mixture was stirred overnight at 65° C., cooled, and excess sodium hydride decomposed by careful dropwise addition of water (100 ml.). The resulting mixture was partially concentrated and extracted with chloroform. The agueous layer was cooled in an ice bath and acidified to pH3 with 2.5 M hydrochloric acid. The mixture was immediately extracted combined organic extracts dried over sodium sulfate. Evaporation of the filtered solution gave benzyl 2acetamido- 3(D -O-1-carboxyethyl)- 2-deoxy- 5,6-O-isopropylidene β-D-glucofuranoside as a slightly colored gummy solid; yield 1.92 g. (85%). The 300 MHz NMR spectrum in dimethylsulfoxide- d$_6$ was in accord with the desired structure.

Step B: Preparation of benzyl 2-acetamido- 2-deoxy-5,6 -O-isopropylidene-3-O-(D-2propionyl-L-alanyl-D-isoglutamine benzyl ester)β-D-glucofuranoside To a solution of benzyl 2-acetamido-3 -O-(D-1-carboxyethyl)-2deoxy-5, 6-O- isopropylidene β-D glucofuranoside (1.88 g., 4.44 mmol) in dry N,N-dimethylformamide (15 ml.) at −15° C. were added successively N methylmorpholine (0.49 ml.) and isobutyl chloroformate (0.58 ml). After stirring 5 min. 15° C., a precooled solution of L-alanyl-D-isoglutamine benzyl ester hydrochloride (1.53 g., 4.45 mmol) and N-methylmorpholine (0.49 ml.) in dry N,N-dimethylformamide (10 ml.) was added. The mixture was stirred for 4 hrs. at −15° C. with exclusion of moisture. After the temperature was increased to 0° C., 2.5 M agueous potassium hydrogencarbonate (8 ml.) was added, and the mixture was stirred for 30 min. at ° C. Since no precipitation of product occurred upon addition of (200 ml.), the mixture was brought to pH7 with 2.5 M hydrochloric acid. After evaporation, the residue was partitioned between chloroform and water, the combined organic extracts washed with water, dried over magnesium sulfate, and evaporated to a syrup that was dissolved in the minimal volume of chloroform. The solution was applied to a column of silica gel (Merck No. 7734) that was eluted with initially 24:1 and subseguently 9:1 chloroform methanol. The fractions containing the desired product were combined and evaporated to a syrup that solidified upon trituration with diethyl ether. The amorphous solid was filtered and dried in vacuo to afford benzyl 2-acetamido-2-deoxy- 5,6-O-isopropyl idene-3-O-(D-2-propionyl-L-alanyl-D-isoglutamine benzyl ester)-β-D-glucofuranoside; yield 2.0 g. (63%); 1° (c 1, chloroform). The 300 MHz NMR spectrum in dimethylsulfoxide d was in accord with the desired structure.

Analysis: Calculated for $C_{36}H_{48}N_4O_{11} \cdot \frac{1}{2}H_2O$ (721.82): C, 59.90; H, 6.84;N, 7.76; Found: c, 59.68; H, 6.74; N, 782.

Step C: Preparation of benzyl 2-acetamido- 2deoxy-3-O- (D-2-propionyl-L-alanyl-D-isoglutamine benzyl ester)-β-D-glucofuranoside A mixture of benzyl 2-acetamido- 2-deoxy- 5,6-O-isopropylidene-3-O-(D- 2-propionyl-L- alanyl -D-isoglutamine benzyl esterside (1.8 g., 2.5 mmol) in 65% agueous acetic acid (100 ml.) was stirred at 40° C. until thin layer chromatography investigation (9:1 chloroform methanol as developing system) indicated complete conversion to a slower-moving material. The mixture was then evaporated, with traces of acetic acid being removed by several coevaporations with toluene. The residue was triturated with diethyl ether, the resulting solid filtered, washed with ether and dried in vacuo over 2-acetamido- 2-deoxy- 3-O- (D- 2-propionyl-L-alanyl-D-isoglutamine benzyl ester)-β-D-glucofuranoside as an amorphous solid; yield 1.63 g. (96%); [α]$_D$ −73° (c 1, chloroform). The 300 MHz NMR spectrum in dimethylsulfoxide-d $_6$ was in accord with the desired structure.

Analysis: Calculated for $C_{33}H_{44}N_4O_{11} \cdot \frac{1}{2}H_2$(681.75): C, 58.14; H, 6.65; N, 8.22. Found: C, 57.91, H, 6.49; N, 8.15.

Step D: Preparation of benzyl 2-acetamido-5,6-di-O-acetyl- 2deoxy 3-O-(D- 2propionyl-L-alanyl-D-isoglutamine benzyl ester) B D-glucofuranoside To a solution of benzyl 2acetamido-2-deoxy-3-O-(D-2-propionyl-L-alanyl-D-isoglutamine benzyl ester) β-glucofuranoside (500 mg., 0.74 mmol) in dry pyridine (6 ml ) at room temperature was added acetic anhydride (4 ml.). The mixture was kept at room temperature until thin layer chromatography investigation (9:1 chloroform methanol as developing system) indicated complete conversion to a faster moving material. The formation of intermediate mono-O-acetates was observed. The mixture was then evaporated and coevaporated several times with toluene. The residue was dissolved in the minimal volume of chloroform and the solution passed through a short column of silica gel (Merck No. 7734) to remove small amounts of impurities. Benzyl 2-acetamido-5,6- di -O-acetyl-2-deoxy- 3-O-(D-2propionyl-L-alanyl-D-isoglutamine benzyl ester)-β-D-glucofuranoside was crystallized from ethanoldiethyl ether; yield 377 mg. (67%); m.p. 164 °–166° C., [α]$_D$ −69° (c 1, chloroform). The 300 MHz NMR spectrum in dimethylsulfoxide d$_6$ was in accord with the desired structure.

Analysis: Calculated for $C_{37}H_{48}N_4O_{13}$(756.8): C, 58.72; H, 6.39; N, 7.40 Found: C, 58.33; H, 6.41; N, 7.45

Step E: Preparation of 2acetamido -5,6-di-O-acetyl-2-deoxy- 3-O-(D-2-propionyl-L-alanyl-D- isoglutamine)-D-glucofuranose A solution of benzyl 2acetamido 5,6-di-acetyl 2 deoxy 3 0 (D- 2 propionyl-L-alanyl-D-isoglutamine benzyl ester)-β-glucofuranoside (200 mg., 0.26 mmol) in glacial acetic acid (5 ml.) was hydrogenolyzed overnight at atmospheric pressure and room temperature in the presence of palladium (added as PdO, 200 mg.). The reaction mixture was filtered through Celite, the filtrate evaporated, and coevaporated several times with water and finally with toluene. The residue was taken up in a small volume of methanol, filtered to remove undissolved materials, and the product precipitated by addition of diethyl ether. The solid was filtered, washed with ether, and dried in vacuo over phosphorous pentoxide. The solid was dissolved in water and lyophilized to afford 2-acetamido- 5, -di-O-acetyl-2-deoxy- 3-O-(D-2-propionyl-L-alanyl- isoglutamine) D-glucofuranose as a white amorphous solid; yield 130 mg. (86%). The 300 MHz NMR spectrum in deuterium oxide was in accord with the desired structure.

EXAMPLE 2

Preparation of 2-acetamido-5-O-acetyl-2-deoxy-3-O-(D-2-propionyl-L-alanyl-D-isoglutamine)-6stearoyl -O-D-glucofuranose Step A: Preparation of benzyl 2acetamido-5-O-acetyl-2-deoxy-3 0 (D-2-propionyl-L-alanyl-βD-isoglutamine benzyl ester) 6 0-stearoyl -β-D-glucofuranoside To a solution of benzyl 2-acetamido- 2deoxy-3-O-(D-2-propionyl-L-alanyl-D-isoglutamine benzyl ester)-α-D-glucofuranoside (250 mg., 0.37 mmol) in dry pyridine (10 ml.) was added stearoyl chloride (0.31 ml., 0.93 mmol). The reaction mixture was stirred for 18 hrs. at room temperature with exclusion of acetic anhydride for 24 hrs. at room temperature. The mixture was then evaporated and coevaporated several times with toluene. The residue was dissolved in the minimal volume of chloroform, and the solution was applied to a column of silica gel (Merck No. 7734) and elution was effected with 30:1 chloroform/methanol. Further purification was achieved by thick layer chromatography on plates (1.000 mm) of silica gel GF$_{254}$ (Analtech) with 9:1 chloroform methanolwith ethyl acetate. Evaporation gave a chromatographically homogeneous solid that was hydrogenolyzed as described in Step B. The 300 MHz NMR spectrum in dimethylsulfoxide d6 was in accord with the desired structure.

Step B: Preparation of 2-acetamido- 5-O-acetyl-2-deoxy- 3-O-(D-2propionyl-L-alanyl-D-isoglutamine)-6-O-stearoyl-D-glucofuranose A solution of the solid obtained in Step A in glacial acetic acid (5 ml.) was hydrogenolyze 18 hrs. at atmospheric pressure and room temperature in the presence of palladium (added as PdO, 150 mg.). The reaction mixture was filtered through Celite, the filtrate evaporated, and coevaporated several times with water and finally with toluene. The residue was triturated with diethyl ether, the solid filtered, washed with ether, and dried in vacuo over phosphorous pentoxide. 2-Acetamido- 5-O-acetyl- 2-deoxy-3-O-(D-2-propionyl-L-alanyl-L-isoglutamine)-6stearoyl-D-glucofuranose was obtained as an amorphous solid; yield 22 mg. (7.4% based on benzyl 2-acetamido-2d6oxy-3-O-(D- 2-propionyl-L-alanyl-D-isoglutamine benzyl ester)-β-D-glucofuranoside). The 300 MHz NMR spectrum in dimethylsulfoxide d$_6$ was in accord with the desired structure.

EXAMPLE 3

Preparation of 2-acetamido- 5-O-acetyl-6-O-behenoyloxy-isobutyryl2-deoxy-3-O-(Disoglutamine)-D-glucofuranose Step A: Preparation of benzyl 2 acetamido 6-0 behenoyloxyisobutyryl- 2-deoxy-3-O-(D- 2-propionyl-L-alanyl-D-isoglutamine)-D-glucofuranose benzyl ester)-β-D-glucofuranoside To a solution of behenoyloxyisobutyric acid (159 mg., 0.37 mmol) in dry N,N- dimethylformamide (4 ml.) was added 4-dimethylaminopyridine (5 mg.) and benzyl 2-acetamido- 2-deoxy-3-O-(βD-2 propionyl-L-alanyl-D-isoglfuranoside (250 mg., 0.37 mmol). The mixture was cooled in an ice-bath and N,N' dicyclohexylcarbodiimide imide (DCC) (77 mg.) was added. The reaction mixture was stirred overnight at room temperature. Dichloromethane was added to the mixture to achieve solution. A second addition of behenoyloxyisobutyric acid (159 mg.) and DCC (77 mg.) was made and the mixture stirred overnight at room temperature. Again sufficient dichloromethane was added to cause solution. After a third addition of the acid and DCC and stirring overnight a room temperature, the reaction mixture was concentrated, the solid taken up in dichloromethane, washed twice with 0.5 M hydrochloric acid, once with saturated agueous sodium bicarbonate, the organic layer filtered and dried (sodium sulfate). The solid obtained upon evaporation was dissolved in the minimal volume of chloroform, and the solution was applied to a column of silica gel (Merck No. 7734) that was eluted with 30:1 chloroform methanol. Evaporation of the appropriate fractions gave benzyl 2-acetamido- 6 -O--behenoyloxyisobutyryl- 2-deoxy- 3-O-(D-2-propionyl-L-alanyl-D-isolutamine benzyl ester)-β-D-glucofuranoside as a solid; yield 80 mg. (20%).

Step B: Preparation of benzyl 2-acetamido-5-O-acetyl-6behenoyloxyisobutyryl-2 deoxy-3 -O-(D-2-propionyl-L-alanyl-D-isoglutamine benzyl ester)-β-D-glucofuranoside To a solution of benzyl 2-acetamido-6-O-behenoyloxyisobutyryl-2-deoxy-3-O-(D-2-propionyl--alanyl-D-isoglutamine benzyl ester)-β-D-glucofuranoside (80 mg.) in dry pyridine (1 ml.) was added acetic anhydride (0.6 ml.). The reaction mixture was allowed to stand overnight at room temperature, evaporated, and coevaporated several times with toluene. The residue was dissolved in the mto a column of silica gel (Merck No. 7734) that was eluted with 35:1 chloroform methanol. The appropriate fractions were combined and evaporated to give benzyl 2-acetamido-5-O-acetyl- 6-O-behenoyloxyisobutyryl 2-deoxy-3-O-(D-2-propionyl-L-alanyl-D-isoglutamine benzyl ester)-8D glucofuranoside as a solid; yield 73 mg. (88%). The 300 MHz NMR spectrum in dimethylsulfoxide-d was in accord with the desired structure.

Step C: Preparation of the 2-acetamido-5-O-behenoyloxyisobutyryl-2-deoxy 3 -acelyl-6-O-(D-2-propionyl-L-alanyl-D-isoglutamine)-D-glucofuranose A solution of benzyl 2-acetamido-5-O-acetyl-6-O-behenoyloxyisobutyryl-2-deoxy-3-O-(D-2-propionyl-L-alanyl-D-isoglutamine benzyl ester)-β-D-gluco-furanoside (70 mg.) in glacial acetic acid (5 ml.) was hydrogenolyzed for 24 hrs. at atmospheric pressure and room temperature in the presence of palladium (added as PdO, 110 mg.). The reaction mixture was filtered through Celite, the filtrate evaporated, and co-evaporated several timetoluene. The residue was applied to a column of silica gel (Merck No. 7734) that was eluted with initially 9:1 chloroform-methanol and subseguently 80:20:2 chloroform methanol-water. Evaporation of the appropriate fractions gave a solid that was dried in vacuo over phosphorous pentoxide. 2 Acetamido-5 -O-acetyl- 6-O-behenoyloxyisobutyryl-2-deoxy-3-O-(D-2-propionyl-L-alanyl-D-isoglutamine-D-glucofuranose was obtained in 54% yield (32 mg.). The 300 MHz NMR spectrum in dimethylsulfoxide $d_6$ was in accord with the desired structure.

It is reasonably believed on the basis of the data, that the disclosed compounds herein, either alone, or in combination with an anti-AIDS drug, will provide a human host, who is immunocompromised as a result of infection or contact with an AIDS-related virus, with enhanced host resistance to opportunistic bacterial, fungal, or viral infection, including the conditions of Kaposi's sarcoma and Pneumocystis pneumonia.

What is claimed is:

1. A composition for enhancing host resistance against opportunistic bacterial, fungal or viral infection in a human host immunocompromised by an AIDS-related virus comprising a compound of the formula:

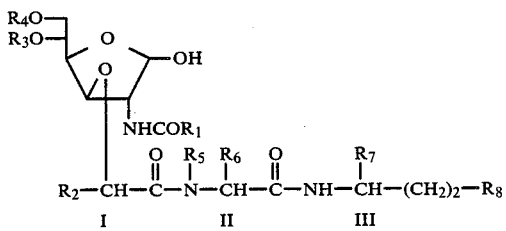

wherein:

$R_1$ is $C_{1-7}$ alkyl, substituted $C_{1-7}$ alkyl; phenyl; or substituted phenyl;

$R_2$ is hydrogen; or $C_{1-10}$ alkyl;

$R_3$ and $R_4$ may be the same independently acyl of the formula:

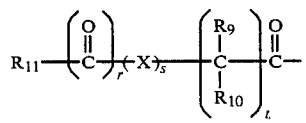

where X is -O-, -S-, or $R_9$, $R_{10}$, and $R_{12}$ may be the same or different and are each independently hydrogen; $C_{1-20}$ alkyl; $C_{1-20}$ alkylcarbonyloxy; amino; benzyl; $C_{1-20}$ alkylamido; alkoxymethyl; or $C_{1-20}$ alkylamido;

r is 0 or 1; s is 0 or 1; and t is 0-20, provided that s may only be 0 when r and t are greater than 0, or when r is 0 and $R_{11}$ is amino, phenyl, substituted phenyl, 1-adamantyl, or heterocycle selected from the gorup consisting of 2- or 3-furyl, 2- or 3-thienyl, 2- or 3-pyrrolidinyl, 2-, 3-, or 4-pyridyl, and 1-tetrazolyl, said heterocycle optionally substituted with $C_{1-20}$ alkylcarbonyl; and $R_{11}$ is hydrogen; C1-30 alkyl; $C_{2-30}$ alkenyl; $C_{1-30}$ alkoxy; phenyl; $C_{1-20}$ alkylsulfonyl; or cholesteryl; and $R_4$ may additionally be hydrogen;

$R_5$ is hydrogen; or $R_5$—$R_6$ together is -$CH_2$-$CH_2$-$CH_2$;

$R_6$ is hydrogn; $C_{1-7}$ alkyl; hydroxymtehyl; mercaptomethyl; benzyl; or substituted benzyl;

$R_7$ and $R_8$ may be the same or different and are each ndependently COOR or CONR' R", where R is hydrogen or $C_{1-7}$ alkyl, and R' and R" are each independently hydrogen or $C_{1-3}$ alkyl;

when $R_2$ is $C_{1-10}$ alkyl, the stereochemistry at asymmetric p1 when $R_6$ is not hydrogen, the stereochemistry at asymmetric center I can be either D or L;

when $R_2$ is $C_{1-3}$not hydrogen, the stereochemistry at center II is L; the stereochemistry at asymmetric center III is D; or pharmaceutically acceptable salts thereof; and an antiviral anti-AIDS drug selected from the group consisting of azidothymidine, ansamycin, ribavirin, deoxycytidine, HPA-23, AL-721, and foscarnet, ina physiologically acceptable medium in an amount effective to impart resistance against bacterial, fungal or viral infection.

2. The composition according to claim 1 wherein the compound is a preparation of 2-acetamido5, 6-di-O-acetyl-2-deoxy-3-O-(D-2-propionyl-L-alnayl-D-isoglutamine)-D-glucofuranose.

3. The composition according to claim 1 wherein the compound is a preparation of 2-acetamido-5-O-acetyl-2-deoxy-3-O-(D-2-propionyl-L-alanyl-D-isoglutamine)-6-0-stearoyl-D-glucofuranose.

4. The composition according to claim 1 wherein the compound is a preparation of 2-acetamido-5-O-acetyl-6-0-behenoyloxyisobutyryl-2-deosy-3-0(D-2-propionyl-L-alanyl-D-isoglutaimen)-D-glucofuranose.

5. A method for enhancing host resistance against opportunistic bacterial, fungal or viral infection in a human host immunocompromised by an AIDS-related virus comprising the step of administering to said host a composition containing a compound according to claim 1.

* * * * *